United States Patent [19]

Lee et al.

[11] Patent Number: 4,568,646

[45] Date of Patent: Feb. 4, 1986

[54] **PREPARATION OF ANTIBIOTIC LL-D05139β FROM CULTURES OF *GLYCOMYCES HARBINENSIS*, GEN. NOV., SP. NOV.**

[75] Inventors: May D. Lee, Monsey; Donald B. Borders, Suffern; David P. Labeda, Monsey; Amedeo A. Fantini, New City, all of N.Y.; Raymond T. Testa, Cedar Grove, N.J.

[73] Assignee: American Cyanamid Company, Stamford, Conn.

[21] Appl. No.: 694,567

[22] Filed: Jan. 24, 1985

Related U.S. Application Data

[62] Division of Ser. No. 488,496, Apr. 25, 1983.

[51] Int. Cl.$^4$ .......................... C12N 1/20; C12R 1/01; C12R 1/04; C12R 1/365; A61K 37/00
[52] U.S. Cl. .................................... 435/253; 435/822; 435/826; 435/872; 514/2

[58] Field of Search ............... 435/253, 822, 826, 872; 424/177

[56] References Cited

PUBLICATIONS

Meyer, J., *Interntl. J. Systemic Bacteriology*, vol. 26(4), pp. 487–493, 1976.
Hasegawa, T. et al, *Interntl. J. Systemic Bacteriology*, vol. 28(2), pp. 304–310 (1978).
Pettit, *Synthetic Peptides*, vol. I, pp. 86 and 87 (1971).
Pettit, *Synthetic Peptides*, vol. II, pp. 128 and 129 (1977).

*Primary Examiner*—Thomas G. Wiseman
*Assistant Examiner*—Jayme A. Huleatt
*Attorney, Agent, or Firm*—Anne Rosenblum; Susan H. Rauch

[57] ABSTRACT

This disclosure describes a new antibacterial and antitumor agent designated LL-D05139β, produced in a microbiological fermentation under controlled conditions using a new genus *Glycomyces harbinensis* gen. nov., sp. nov., and mutants thereof.

6 Claims, 3 Drawing Figures

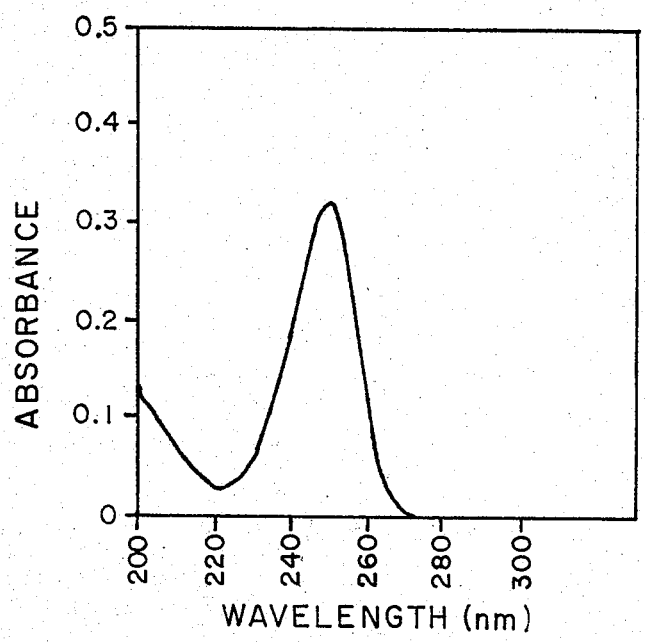
FIGURE I

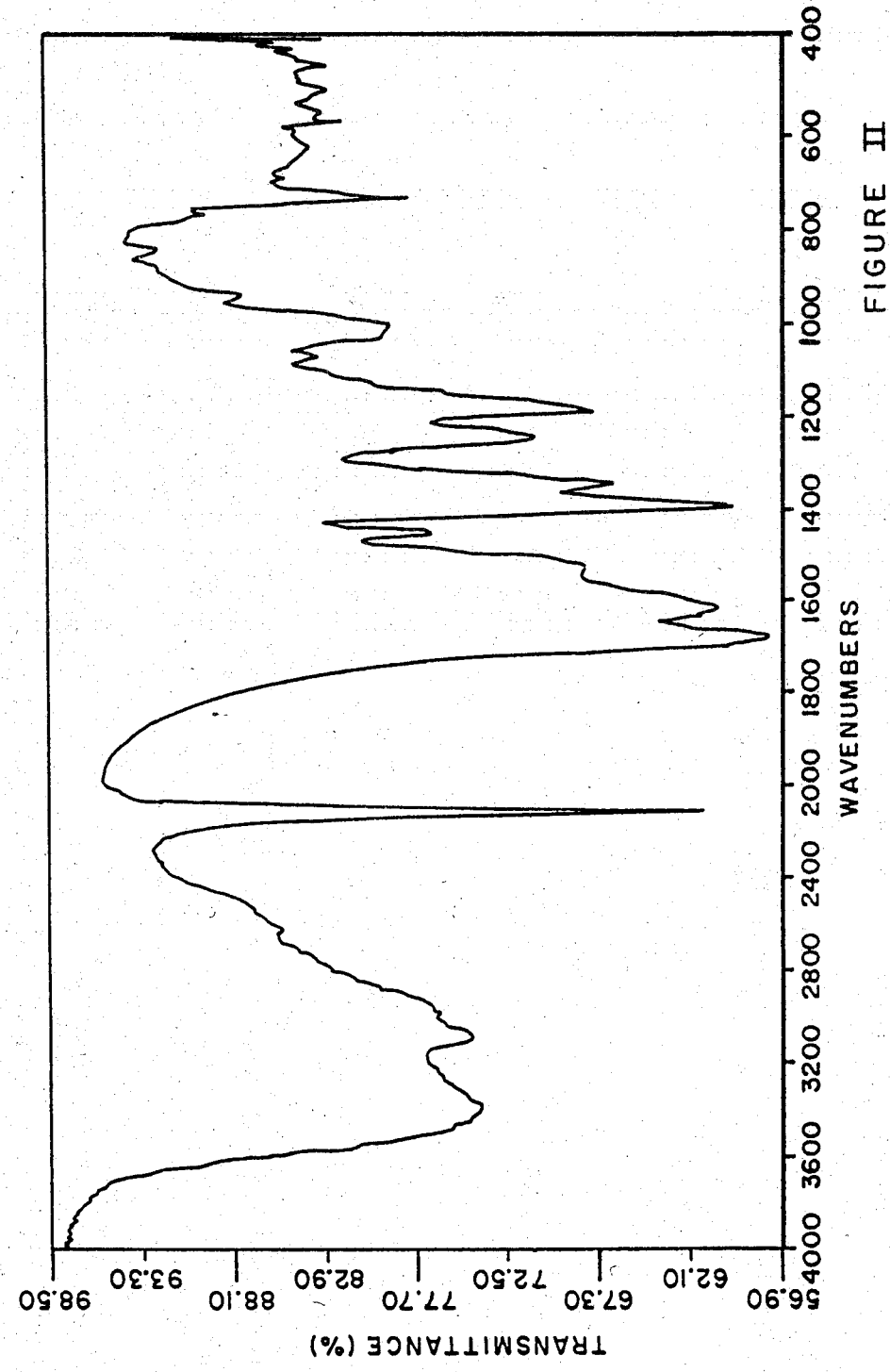

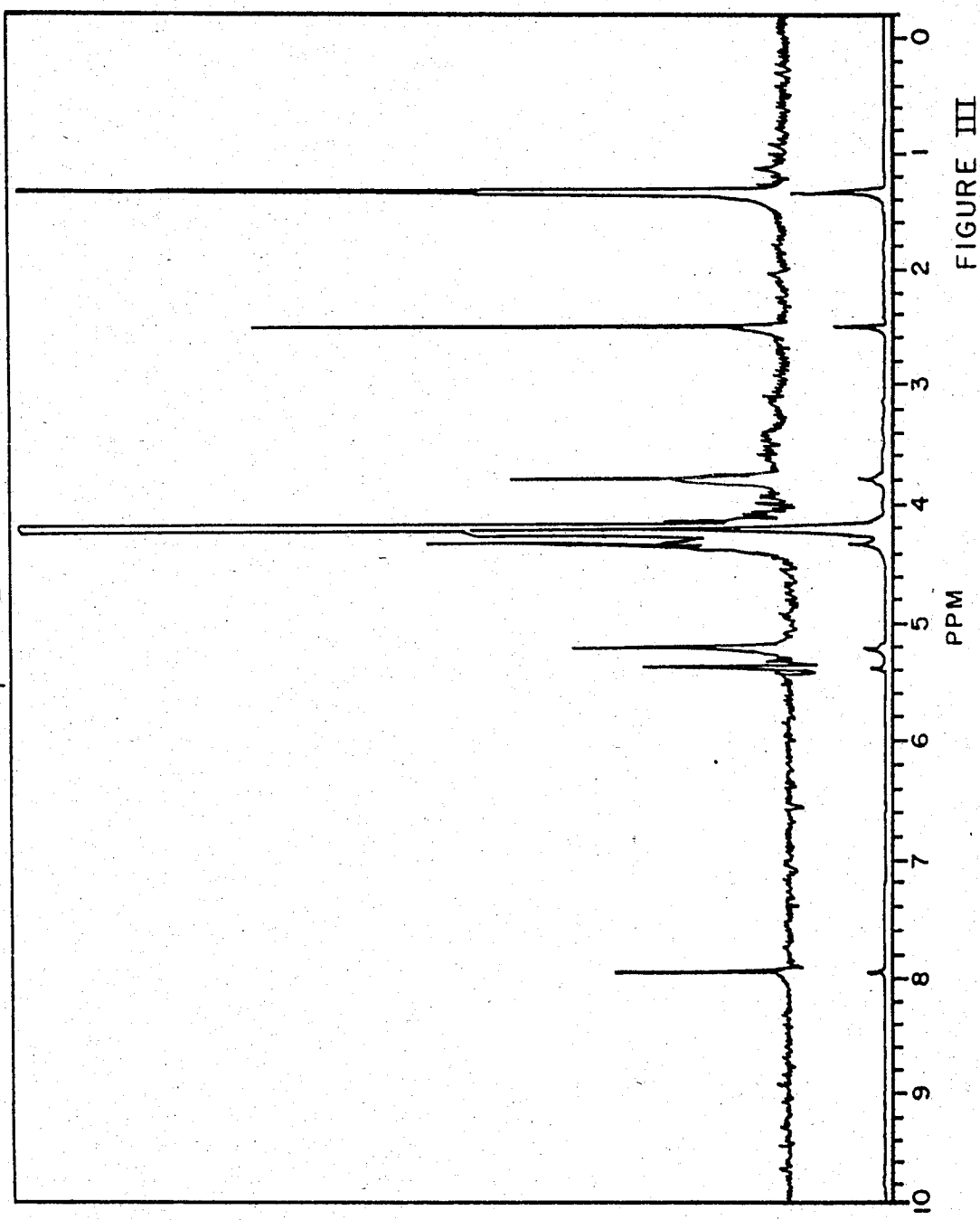

4,568,646

PREPARATION OF ANTIBIOTIC LL-D05139β FROM CULTURES OF GLYCOMYCES HARBINENSIS, GEN. NOV., SP. NOV.

This is a division of application, Ser. No. 488,496, filed Apr. 25, 1983.

BRIEF SUMMARY OF THE INVENTION

This invention relates to a new antibacterial and antitumor agent designated LL-D05139β, to its production by fermentation, to methods for its recovery and concentration from crude solutions and to processes for its purification. The present invention includes within its scope the antibacterial and anti-tumor agent in dilute form, as a crude concentrate and in pure form. The effects of this new agent on specific microorganisms, together with its structure and chemical and physical properties, differentiate it from previously described antibacterial agents.

LL-D05139β has the structure

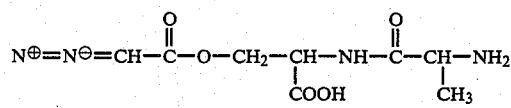

and its chemical abstracts nomenclature is N-L-alanyl-L-serine diazoacetate.

It is related to, but structurally different from, serine (2-amino-3-hydroxypropionic acid) whose structure is

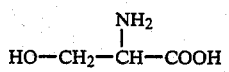

and azaserine (serine diazoacetate) whose structure is

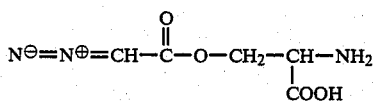

which is a known anti-neoplastic agent.

LL-D05139β is an organic carboxylic acid and thus is capable of forming salts with nontoxic pharmaceutically acceptable cations. Thus salts formed by admixture of the antibiotic free acid with stoichiometric amounts of cations, suitably in a neutral solvent, may be formed with cations such as alkali metals (e.g., sodium, potassium, etc.), alkaline earth metals (e.g., calcium, magnesium, etc.) and ammonium. The cationic salts of LL-D05139β are, in general, water soluble solids relatively insoluble in most common organic solvents.

DETAILED DESCRIPTION OF THE INVENTION

The new antibacterial agent designated LL-D05139β is formed during the cultivation under controlled conditions of a new strain of a new genus and species named Glycomyces harbinensis, gen. nov., sp. nov.

Depending on the fermentation conditions, variable amount of azaserine is coproduced. Under proper cultivation conditions, using defined medium LL-D05139β is produced as the major active component. The physiochemical characteristics of LL-D05139β are as follows:

1. Molecular weight: 244 (FAB-MS).
2. $UV_{max}$ at 250 nm, $E_{1cm}^{1\%} = 646$ (UV spectrum as shown in FIG. I, water solution).
3. IR spectrum (KBr disc) as shown in FIG. II.
4. Optical Rotation: $[\alpha]_D^{26} = +57° \pm 5°$ (C,0.19%, water).
5. $^1$H NMR Spectrum (D$_2$O, ppm from TMS) as shown in FIG. III, 1.56(3H, d, J=7.4 Hz), 4.07(1 H, q. J=7.4 Hz), 4.49(2-3H, m), 5.19(1H, broad s).
6. Decomposes rapidly below pH 5.0, stable in weakly basic solutions.

Acid hydrolysis of LL-D05139 releases one molar equivalent each of L-alanine and L-serine as determined by standard amino acid analysis. Both alanine and serine derived from LL-D05139 have the L-configuration as determined by the well-accepted gas chromatography procedure using n-Lauroyl-L-valine-t-butylamide as stationary phase. See R. Charles et al., J. Chromatography, 112: 121-133 (1975). N-Terminal analysis of LL-D05139β using the Edman degradation procedure followed by HPLC analysis of the PTH-amino acid identified the N-terminal amino acid to be L-alanine. Therefore this agent has been assigned the following structure:

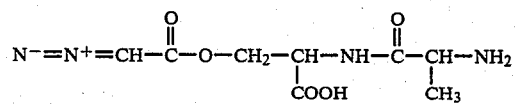

This new antibiotic producing strain was isolated from a soil sample collected in Harbin, China and is maintained in the culture collection of the Lederle Laboratories Division, American Cyanamid Company, Pearl River, N.Y. as culture number LL-D05139. A viable culture of this new microorganism has been deposited with the Culture Collection Laboratory, Northern Utilization Research and Development Division, U.S. Department of Agriculture, Peoria, Ill., has been added to its permanent collection under the accession number NRRL 15337, and is freely available to the public from this depository.

Taxonomic Characterization of Culture LL-D05139

The culture LL-D05139 was taxonomically characterized and identified as the type species of a new genus to be known as Glycomyces harbinensis gen. nov., sp. nov.

Observations were made of the cultural, physiological and morphological features of the culture using methods detailed by E. B. Shirling and D. Gottlieb, Methods for characterization of Streptomyces species., Internat. J. Syst. Bacteriol. 16: 313-340 (1967), and R. E. Gordon, et al., Nocardia colliaca, Nocardia autotrophica, and the nocardia strain., Internat. J. Syst. Bacteriol., 24: 54-63 (1974). Media used in this study were selected from those recommended by T. G. Pridham, et al., A selection of media for maintenance and taxonomic study of Streptomycetes., Antibiotics Ann., 947-953 (1956-57), G. F. Gauze, et al., Problems in the classification of antagonistic actinomycetes., State Publishing House for Medical Literature. Medgiz Moscow (1957) and R. E. Gordon, et al., vide supra for the taxonomic study of actinomycetes and soil bacteria. Chemical composition of the cell walls of the culture was determined using the method of H. A. Lechevalier, et al., Chemical composition as a criterion in the classification of Actinomycetes., Adv. Appl. Microbiol. 14: 47-72

(1971). Phospholipid patterns were determined using the method of M. P. Lechevalier, et al., Chemotaxonomy of aerobic actinomycetes: phospholipid composition., Biochem. Syst. Ecol., 5: 249–260 (1977). Details are recorded in Tables I–VI, and a general description of the culture is given below. Underscored descriptive colors are taken from K. L. Kelly and D. B. Judd, Color. Universal Language and Dictionary of Names, Nat. Bur. Stand. (U.S.), Spec. Publ. 440, Washington, D.C. (1976) and the accompanying Inter-Society Color Council, Nat. Bur. Stand. Centroid Color Charts.

The data observed for this culture were compared with data published for known genera of the Actinomycetales M. Goodfellow, et al., Numerical taxonomy of Actinomadura and related actinomycetes., J. Gen. Microbiol., 112: 95–111 (1979), T. Hasegawa, et al., New Genus of the Actinomycetales: Actinosynnema gen. nov., Internat. J. Syst. Bacteriol., 28 (2): 304–310(1978), and J. Meyer, Nocardiopsis, a new genus of the order Actinomycetales., Internat. J. Syst. Bacteriol., 26 (4): 487–493(1976). Isolate LL-D05139 bears no close resemblance to any of the known actinomycete genera, with Nocardiopsis being the most closely related taxon from a morphological standpoint. The whole-cell chemistry of LL-D05139 is Type II-D (meso-DAP, and arabinose and xylose as the characteristic sugars). The phospholipid pattern of this culture, as observed by thin-layer chromatography, represents a very unusual pattern for the Type P-I group. The Type II-D whole cell analysis, usually typical of Micromonospora, and the unusual Type P-I phospholipid pattern are totally novel for a microorganism possessing the morphology of this culture. Based on these observations, the culture is assigned to a new genus designated as Glycomyces. The species name *harbinensis* refers to the site in Harbin, China where the soil sample was collected from which this culture was isolated.

Micromorphology

Spores are formed in very short straight chains on rudimentary aerial sporophores. The spores are cylindrical in shape, 0.45 to 0.55 microns by 0.98 to 1.06 microns, and have a smooth surface.

Cell Wall Composition

Whole cell hydrolysates of this culture contain the meso-isomer of diaminopimelic acid, arabinose and xylose as the characteristic sugars. The culture has an unusual variation of the Type P-I phospholipid pattern and contains phosphatidyl glycerol, phosphatidyl inositol and phosphatidyl inosityl mannosides. This phospholipid composition has not been reported for any other genus in the Actinomycetales to date.

Amount of Growth

Good growth observed on NZ-amine-starch-glucose agar (ATCC Medium 172) and yeast extract-malt extract agar; moderate growth observed on Benedict's agar, Bennett's agar, calcium malate agar, Czapek's sucrose agar, Gauze No. 1 agar, Hickey-Tresner agar, and oatmeal agar; poor growth observed on inorganic salts-starch agar; no growth observed on tomato paste-oatmeal agar.

Vegetative Mycelium

On media where good growth occurred, the vegetative mycelium was observed to be raised and convoluted and was generally yellowish white in color. A fetid odor was observed on several media.

Aerial Mycelium and Spore Color

Aerial mycelium absent on most media; very sparse white mycelia when present.

Soluble Pigments

Absent on most media; yellowish pigment on NZ-amine-starch-glucose agar.

Physiological Reactions

No melanin pigments on peptone-iron agar and tyrosine agar (ISP-7); strong peptonization of litmus milk; no proteolysis of nutrient gelatin; weak to no reduction of nitrate, no hydrolysis of tyrosine or xanthine; strong hydrolysis of adenine, and hypoxanthine; weak hydrolysis of starch; strong hydrolysis of esculin; no hydrolysis of urea. Carbohydrate utilization as per the method of T. G. Pridham and D. Gottleib. The utilization of carbon compounds by some Actinomycetales as an aid for species determination. J. Bacteriol., 56: 107–114 (1948): good utilization of galactose, glucose, glycerol, lactose, maltose, mannitol, trehalose and xylose; moderate utilization of arabinose, fructose, mannose, rhamnose and sucrose; poor utilization of melibiose and salicin; no utilization of adonitol, dulcitol, inositol, melezitose, raffinose and sorbitol. Acid production from carbohydrates by the method of R. E. Gordon et al. (vide supra); Good acid production from arabinose, fructose, galactose, glucose, glycerol, maltose, mannitol, mannose, rhamnose, salicin, sucrose and trehalose; weak acid production from lactose, melezitose and raffinose. Utilization of organic acids by the method of R. E. Gordon et al. (vide supra); utilization of lactate and malate; no utilization of benzoate, citrate, mucate and oxalate.

TABLE I

| Cultural Characteristics of Glycomyces harbinesis LL-D01539 | | | | |
|---|---|---|---|---|
| Incubation 14 days | | | Temperature: 28° C. | |
| Medium | Amount of Growth | Aerial Mycelium and/or Spores | Soluble Pigment | Reverse Color |
| Benedict's agar | Moderate | Smooth, somewhat plicate vegetative mycelia, 92. yellowish white; no aerial mycelia or spores; fetid odor | None | 92. yellowish white |
| Bennett's agar | Moderate | Raised waxy white growth; no aerial mycelia; fetid odor | None | 92. yellowish white |
| Calcium Malate agar | Moderate to good | White vegetative mycelia with white aerial mycelia | None | — |
| Czapek's Sucrose agar | Good to moderate | White vegetative mycelia with copious white aerial mycelia and spores | None | 89. pale-yellow |

TABLE I-continued

Cultural Characteristics of *Glycomyces harbinesis* LL-D01539

Incubation 14 days  
Temperature: 28° C.

| Medium | Amount of Growth | Aerial Mycelium and/or Spores | Soluble Pigment | Reverse Color |
|---|---|---|---|---|
| Gauze No. 1 agar | Moderate | Flat, dull colorless vegetative mycelia, aerial mycelia | None | — |
| Hickey Tresner agar | Moderate | Plicate, waxy growth, 92. yellowish white, no aerial mycelia; fetid odor | None | — |
| Inorganic Salts-Starch agar | Moderate to poor | Flat, colorless to white vegetative growth with sparse white aerial mycelia around edges of colonies | None | Colorless |
| NZ—amine-Starch Glucose agar | Good | Raised, ridged vegatative growth 92. yellowish white, trace white aerial mycelia | yellowish | — |
| Oatmeal agar | Moderate | Flat colorless to white vegetative growth with no apparent aerial mycelia | None | — |
| Tomato Paste-Oatmeal agar | None | | | |
| Yeast Extract-Malt Extract agar | Good | Plicate, raised growth, 92. yellowish white; no aerial mycelia | None | 89. pale yellow |

TABLE II

Micromorphology of *Glycomyces harbinesis* LL-D05139

| Medium | Aerial Mycelium and/or Sporiferous Structures | Spore Shape | Spore Size | Spore Surface |
|---|---|---|---|---|
| Czapek's Sucrose agar | Rudimentary aerial sporophores carrying relatively short straight chains of mature spores | Cylindrical | 0.50 ± 0.05 micron × 1.02 ± 0.04 micron | Smooth |

TABLE III

Physiological Reactions of *Glycomyces harbinensis* LL-D05139

| Medium | Incubation Period | Amount of Growth | Physiological Reaction |
|---|---|---|---|
| Peptone-Iron agar | 7 Days | Good | No pigment |
| | 14 Days | Good | No pigment |
| Tyrosine agar | 7 Days | Good | Slight reddish pigment |
| | 14 Days | Good | Slight reddish pigment |
| Litmus Milk | 14 Days | Good | Strong peptonization |
| | 28 Days | Good | Strong peptonization |
| Nutrient Gelatin | 14 Days | Good | No proteolysis |
| | 28 Days | Good | No proteolysis |
| Nitrate Broth | 14 Days | Good | No reduction |
| | 28 Days | Good | Weak reduction |
| Adenine Agar | 14 Days | Good | Hydrolysis |
| | 28 Days | Good | Strong hydrolysis |
| Hypoxanthine agar | 14 Days | Good | Hydrolysis |
| | 28 Days | Good | Strong hydrolysis |
| Tyrosine agar | 14 Days | Good | No hydrolysis |
| | 28 Days | Good | No hydrolysis |
| Xanthine agar | 14 Days | Good | No hydrolysis |
| | 28 Days | Good | No hydrolysis |
| Urea broth | 28 Days | Good | No decomposition |
| Esculin broth | 14 Days | Good | Strong hydrolysis |
| Starch agar | 14 Days | Good | Weak hydrolysis |

TABLE IV

Carbon Source utilization of Glycomyces harbinensis LL-D05139 on ISP-9 Carbohydrate Utilization Medium Incubation: 28 Days  
Temperature: 28° C.

| Carbon Source | Utilization |
|---|---|
| Adonitol | 0 |
| l-Arabinose | 2 |
| Dulcitol | 0 |
| Fructose | 2 |
| d-Galactose | 3 |
| d-Glucose | 3 |
| Glycerol | 3 |
| i-Inositol | 0 |
| Lactose | 3 |
| Maltose | 3 |
| d-Mannitol | 3 |
| d-Mannose | 2 |
| d-Melezitose | 0 |
| d-Melibiose | 1 |
| d-Raffinose | 0 |
| l-Rhamnose | 2 |
| Salicin | 1 |
| Sorbitol | 0 |
| Sucrose | 2 |
| d-Trehalose | 3 |
| d-Xylose | 3 |
| Negative control | 0 |

*3 = Good Utilization  
*2 = Fair Utilization  
1 = Poor Utilization  
0 = No Utilization

TABLE V

Acid Production from Various Carbohydrates by *Glycomyces harbinensis* LL-D05139 on Gordon's Basal Inorganic nitrogen Medium Temperature: 28° C.

| Incubation: 28 Days Carbon Source | Acid Production 7 Days | 28 Days |
|---|---|---|
| Adonitol | — | — |
| l-Arabinose | + | + |
| Dulcitol | — | — |
| Fructose | + | + |
| d-Galactose | + | + |
| d-Glucose | + | + |
| Glycerol | + | + |
| i-Inositol | — | — |

TABLE V-continued

Acid Production from Various Carbohydrates by
Glycomyces harbinesis LL-D05139 on Gordon's
Basal Inorganic nitrogen Medium Incubation: 28 Days  Temperature: 28° C.

| Carbon Source | Acid Production 7 Days | 28 Days |
|---|---|---|
| Lactose | ± | ± |
| Maltose | + | + |
| d-Mannitol | + | + |
| d-Mannose | + | + |
| d-Melezitose | − | ± |
| d-Melibiose | − | − |
| d-Raffinose | − | ± |
| l-Rhamnose | ± | + |
| Salicin | + | + |
| Sorbitol | − | − |
| Sucrose | + | + |
| d-Trehalose | + | + |
| d-Xylose | + | − |
| Negative control | − | − |

+ = Positive response
− = Negative response
± = Weak Positive Response

TABLE VI

Utilization of Organic Acids by Glycomyces harbinensis
LL-D05139 on Gordon's Modification of Koser's Basal Agar
(Koser's Citrate Agar)

Incubation: 28 Days  Temperature: 28° C.

| Carbon Source | Utilization |
|---|---|
| Benzoate | − |
| Citrate | − |
| Lactate | + |
| Malate | + |
| Mucic Acid | − |
| Oxalate | − |
| Succinate | − |

+ = Positive response
− = Negative response

It is to be understood that for the production of this antibacterial agent the present invention is not limited to this particular organism or to organisms fully answering the above growth and microscopic characteristics, which are for illustrative purposes only. In fact, it is desired and intended to include in the term "*Glycomyces harbinensis* gen. nov., sp. nov., NRRL 15337" the natural (spontaneous) mutants of this organism as well as induced mutants produced from this organism by various mutagenic means known to those skilled in the art, such as exposure to X-ray radiation, ultraviolet irradiation, nitrogen mustard, actinophages, nitrosamines and the like. It is also desired and intended to include inter- and intraspecific genetic recombinants produced by genetic techniques known to those skilled in the art, such as, for example, conjugation, transduction, and genetic engineering techniques.

This antibacterial agent is active in vitro against gram-positive and gram-negative bacteria when tested by the standard agar dilution procedure with Mueller-Hinton agar, and an inoculum of each test organism of approximately $10^4$ colony-forming units delivered by a Steers replicating device. The minimal inhibitory concentration (mcg/ml) was defined as the lowest concentration of antibiotic LL-D05139$\beta$ that inhibited visible growth after 18 hours incubation of 35° C. The results are given in Table VII.

TABLE VII

In vitro Antibacterial Activity of LL-D05139$\beta$

| Organism (Name & Number) | | Minimal Inhibitory Concentration (mcg/ml) |
|---|---|---|
| Escherichia coli | Stfd-79-20 | 8 |
| " | #31 | 4 |
| " | ATCC 25922 | 8 |
| Klebsiella pneumoniae | Stfd-79-6 | 128 |
| Klebsiella pneumoniae | SSC-78-1 | 128 |
| | AD | 4 |
| Enterobacter aerogenes | Stfd-79-14 | 128 |
| Enterobacter cloacae | K-79-16 | 128 |
| Serratia sp | TU1-78-15 | 64 |
| Serratia marcescens | QHC-77-2 | 32 |
| Proteus morganii | K-79-25 | 64 |
| Proteus rettgeri | N-76-1 | 16 |
| Providencia stuarti | SSC-80-78 | 64 |
| Providencia stuarti | K-81-29 | 64 |
| Salmonella sp. | QHC-77-3 | 4 |
| Pasteurella multocida | LL #117 | 64 |
| Acinetobacter calcoaceticus | Stfd-79-17 | 512 |
| Acinetobacter calcoaceticus | K-77-1 | 128 |
| Pseudomonas aeruginosa | SSC-78-13 | 512 |
| Pseudomonas aeruginosa | 12-4-4 | 128 |
| Pseudomonas aeruginosa | ATCC 27853 | 128 |
| Staphylococcus aureus | SSC-79-18 | 16 |
| Staphylococcus aureus | FU-79-2 | 16 |
| Staphylococcus aureus | ATCC 25923 | 16 |
| Enterococcus sp. | OSU-75-1 | 64 |
| Enterococcus sp. | SM-77-15 | 64 |
| Micrococcus luteus | PCI-1001 | 4 |
| Bacillus subtilis | ATCC 6633 | 16 |
| Candida albicans | LL #32 | 64 |
| Candida albicans | LL #54 | 128 |

In addition LL-D05139$\beta$ inhibits the growth of transplanted mouse tumors as established by the following test.

Lymphocytic leukemia P388 test

The animals used were DBA/2 mice, all of one sex, weighing a minimum of 17 g and all within a 3 g weight range. There were three animals per test group. The tumor transplant was by intraperitoneal injection of 0.1 ml of dilute ascitic fluid containing $10^6$ cells of lymphocytic leukemia P388. LL-D05139$\beta$ was administered intraperitoneally on days 1,5 and 9 (relative to tumor inoculation) at various doses. The animals were weighed and survivors recorded on a regular basis for 30 days. The ratio of survival time for treated (T)/control (C) animals was calculated. The positive control compound was 5-fluorouracil, given as a 60 mg/kg injection. The criterion for efficacy is T/C×100≧125%. The results of this test appear in Table VIII.

TABLE VIII

Lymphocytic Leukemia P388 Test

| Compound | Dose mg/kg | T/C × 100(%) |
|---|---|---|
| LL-D05139$\beta$ | 200 | 140 |

TABLE VIII-continued

| Lymphocytic Leukemia P388 Test | | |
|---|---|---|
| Compound | Dose mg/kg | T/C × 100(%) |
| | 50 | 150 |
| | 25 | 140 |

Further LL-D05139β was tested in the human tumor clonogenic (stem cell) assay and found to be active against both the human lung (LX-1) carcinoma and the colon(CX-1) carcinoma at 2.0 mcg/ml and higher doses.

Human Tumor Clonogenic Assay

This test was performed essentially by the method of A. Hamburger and S. Salmon, Primary bioassay of human tumor stem cells., Science, 197: 461–463 (1977). Human colon carcinoma (CX-1) and human lung carcinoma (LX-1) tumors were obtained from the National Cancer Institute and propagated in athymic Balb/c mice. Freshly removed tumors were dispersed with trypsin 0.25% and $5 \times 10^4$ lung carcinoma cells or $1 \times 10^5$ colon carcinoma cells in soft (0.3%) agarose medium containing 0.1 ml of test drug were plated onto a solidified (0.5%) agarose base medium in 35 mm grided dishes. Cultures were incubated at 37° C. in a humidified 5% carbon dioxide in air atmosphere. Colonies were counted after 10–11 days. A compound is considered active if the treated/control (T/C) value is ≦30%, representing a 70% cell kill. The results of this test on LL-D05139β appear in Table IX.

TABLE IX

Effect of LL-D05139β on Human Lung and Colon Carcinoma. Clonogenic Assay

| | | Lung Carcinoma | | Colon Carcinoma | |
|---|---|---|---|---|---|
| Compound | Concentration (mgc/ml) | Av. No. of Colonies/ Culture | T/C (%) | Av. No. of Colonies/ Culture | T/C (%) |
| Control | 0 | 590 | | 420 | |
| LL-D05139β | 200 | 78 | 13.0 | | |
| | 20 | 105 | 17.8 | | |
| | 2 | 137 | 23.2 | 67 | 16.0 |

General Procedure for the Production of LL-D05139β

Cultivation of *Glycomyces harbinensis* NRRL 15337 may be carried out in a wide variety of liquid culture media. Media which are useful for the production of LL-D05139β include an assimilable source of carbon such as starch, sugar, molasses, glycerol, etc., an assimilable source of nitrogen such as protein, protein hydrolysates, polypeptides, amino acids, corn steep liquor, etc., and inorganic anion and cation salts such as potassium, sodium, ammonium, calcium, sulfate, carbonate, phosphate, chloride, etc. Trace elements such as boron, molybdenum, copper, etc. are supplied as impurities of other constituents of the media. Aeration in tanks, bottles and flasks is provided by forcing sterile air through or onto the surface of the fermenting medium. Agitation is supplied by a mechanical impeller. An antifoaming agent such as lard oil or silicone defoamer may be used as needed.

General Procedure for the Isolation of LL-D05139β

Due to its poor stability in acid, solutions containing LL-D05139β are kept between pH 7 and pH 9.5 throughout the isolation processes. When defined medium is used for the fermentation, only a trace amount of azaserine is coproduced, LL-D05139β can be recovered from the fermentation by adsorption of the fermentation filtrate on a column of granular carbon and elution from the column by aqueous alcohol mixture. The active preparation is further purified by repeated column chromatography on microcrystalline cellulose, eluting with 1-propanol:water (80:20). When complex medium is used for the fermentation, due to the presence of a large amount of interfering impurities, LL-D05139β cannot be adsorbed from the fermentation filtrate by granular carbon. In this case, the fermentation filtrate is passed through a column of granular carbon to remove azaserine and other impurities. LL-D05139β in the column effluent is then adsorbed onto weak anion-exchange resins such as Amberlite ® IR4-5(OH⊖ or anion-exchanger such as DEAE Sephadex ® or QAE Sephadex ®. The activity can be eluted from the resin or Sephadex ® with dilute aqueous base followed by desalting on a granular carbon column. Antibiotic LL-D05139β is then eluted from the granular carbon column with aqueous alcohol mixtures and further purified as described before.

At the end of each chromatographic step, the partially purified preparations can be conveniently quantitated against analytically pure LL-D05139β using the following HPLC system:

Column: Nucleosil 10, $N(CH_3)_2$, 25 cm (Macherey-Nagel packed column).
Solvent: Methanol:2-propanol:water, 75:5:20.
Detector: 254 nm.
Flow rate: 1.5 ml/minute.
Retention Volume of LL-D05139β = 6 ml.

Also embraced within the purview of the present invention are therapeutic compositions of matter useful for treating bacterial infections and ameliorating cancer diseases in mammals which contain the novel antibiotic of the present invention as the active ingredient thereof. This aspect of the invention includes the novel compositions of matter and the method of treating bacterial infections in mammals when administered in amounts of approximately 100 mg to approximately 10 g per day for a 70 kg subject. The daily dosage may be given as divided doses several times a day. The dosage range is to be adjusted to provide optimum therapeutic response in the mammal being treated.

The instant invention further includes the novel compositions of matter and the method of inducing the regression and/or palliation of leukemia and related cancers in mammals when administered in amounts ranging from about 0.075 mg to about 300 mg per square meter of body surface area per day. The interrelationship of dosages for animals of various sizes and species and humans (based on mg/m² of surface area) is described by Freireich, E. J., et al., Quantitative Comparison of Toxicity of Anticancer Agents in Mouse, Rat, Hamster, Dog, Monkey and Man, Cancer Chemother. Rep., 50 No. 4: 219–244 (May 1966). A preferred dosage regimen for optimum results would be a total treatment dose from about 1.0 mg/m² to about 8 mg/m². Such dosage units are employed that a total of from about 0.5 mg to about 525 mg of the active compound for a subject of about 70 kg of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. The active compound may be specifically administered for the anticancer use by the intravenous, intramuscular, or subcutaneous routes.

Regression and palliation of cancers are attained, for example, using intraperitoneal administration. A single intravenous dosage or repeated daily dosages can be administered. Daily dosages up to about 5 to 10 days are often sufficient. It is also possible to dispense one daily dosage or one dose on alternate or less frequent days. As can be seen from the dosage regimens, the amount of principal active ingredient administered is a sufficient amount to aid regression and palliation of the leukemia or the like, in the absence of excessive deleterious side effects of a cytotoxic nature to the hosts harboring the cancer. As used herein, cancer disease means blood malignancies such as leukemia, as well as other solid and non-solid malignancies such as the melanocarcinomas, lung carcinomas, and mammary tumors. By regression and palliation is meant arresting or retarding the growth of the tumor or other manifestation of the disease compared to the course of the disease in the absence of treatment.

The active compounds may be administered parenterally or intraperitoneally. Solutions or dispersions of the active compound can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersions and by the use of surfactants. The prevention of the action of microorganisms can be brought about by various antibacterial and antifungal agents, for example, parabens, chlorobutanol, phenol, sorbic acid, thimerosal, and the like. In many cases it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount on the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

In therapeutic use, the compounds of this invention may also be administered in the form of conventional oral pharmaceutical compositions. Such compositions may be suitable for oral administration when formulated properly so the compound of the present invention is not exposed to the acid pH of the stomach. The active ingredient may be combined in admixture with a pharmaceutically acceptable carrier, which carrier may take a wide variety of forms depending on the form of preparation desired for administration. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as nontoxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate nontoxic dye, so as to provide a pleasing appearance. In accord with this invention, another example of a suitable oral dosage form is the capsule with the active ingredient specifically formulated to be absorbed in the duodenum.

It is especially advantageous to formulate parenteral and oral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, or (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically-acceptable carrier in dosage unit form as hereinbefore disclosed. A unit dosage form can, for example, contain the principal active compound in amounts ranging from about 0.1 to about 500 mg., with from about 10 to about 500 mg. being preferred. Expressed in proportions for parenteral use, the active compound is generally present in from about 0.1 to about 100 mg/ml of carrier. In the case of compositions containing supplementary active ingredients, the dosages are determined by reference to the usual dose and manner of administration of the said ingredients.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatable with the active ingredient, its use in the therapeutic compositions is contemplated. Supplementary active ingredients can also be incorporated into the compositions.

This invention will be described in greater detail in conjunction with the following non-limiting examples.

EXAMPLE 1

Inoculum Preparation

A typical medium used to grow the primary inoculum was prepared according to the following formula:

| | |
|---|---|
| Dextrose | 1.0% |
| Starch | 2.0% |
| Yeast extract | 0.5% |
| N—Z Amine | 0.5% |
| Calcium carbonate | 0.1% |
| Water qs | 100% |

The pH was adjusted to 7.2 with sodium hydroxide and the medium was sterilized. Mycelial scrapings from an agar slant of *Glycomyces harbinensis* gen. nov., sp. nov., NRRL 15337 were used to inoculate 50 ml of the above sterile medium in a 250 ml flask. The flask was incubated on a rotary shaker at 28° C. and 180-200 rpm for 72 hours. The resulting primary inoculum was used to inoculate a series of 500 ml flasks, each containing 100 ml of the above sterile medium, which were then incubated under the same conditions, providing secondary inoculum.

EXAMPLE 2

Fermentation

A fermentation medium was prepared according to the following formula:

| | |
|---|---|
| Dextrose | 2.0% |
| Sodium Nitrate | 0.1% |
| Ferrous Sulfate heptahydrate | 0.01% |
| Magnesium sulfate heptahydrate | 0.02% |
| Calcium carbonate | 0.5% |
| Water qs | 100% |

The pH was adjusted to 7.4 and the medium was sterilized. Portions of secondary inoculum (Example 1) was used to inoculate 9 liters of the above sterile medium, which was then incubated on a rotary shaker at 180-200 rpm and 28° C. for 6 days at which time the mash was harvested.

EXAMPLE 3

Isolation of LL-D05139β

A 9 liter portion of harvest mash (prepared as described in Example 2 was filtered. The 8200 ml of filtrate (containing 164 ug/ml of LL-D05139β as determined by HPLC) was adjusted to pH 9.0 with the addition of dilute aqueous sodium hydroxide. The filtrate was then cooled in an ice-water bath while being passed through a column packed with 700 ml of activated charcoal, at a flow rate of 16 ml/minute. The column was washed with 700 ml of demineralized water and then eluted with a linear gradient from water to a mixture of water:methanol (4:6) over a period of 6 hours at the rate of 2.6 ml/minute, collecting 5 minute fractions. The elution was continued until 120 fractions were collected. Each fraction was analyzed by thin-layer chromatography (TLC)(with silica gel 60, F254, pre-coated TLC sheets, product of E. Merck Inc.; n-propanol:water (80:20); visualized by F254 quenching and ninhydrin spray; Rf=0.27) and agar diffusion assay against *Escherichia coli*. Fractions 7–57, 58–93 and 94–118 were pooled separately and each pool was concentrated in vacuo to remove the methanol and was then neutralized with dilute hydrochloric acid and freeze-dried, giving respectively 1427 mg (A), 423 mg (B) and 148 mg (C) of yellow solids.

A 748 mg portion of (A) was dissolved in 1.5 ml of water, loaded on a glass column (2.5×110 cm) packed with microcrystalline cellulose and equilibrated in n-propanol:water (80:20). The column was eluted with n-propanol:water (80:20) at a flow rate of 2 ml/minute, collecting 6 minute fractions to a total of 120 fractions. Each fraction was analyzed as described above. Fractions 80–93 and 94–102 were pooled separately. Each pool was azeotroped with water ($\frac{1}{2}$ volume) in vacuo, neutralized with dilute hydrochloric acid and freeze-dried, giving respectively 189 mg of white powder (D) and 58 mg of pale yellow solids (E). Sample (E) was analytically pure LL-D05139β as determined by high pressure liquid chromatography (HPLC) and TLC. Sample (D) contained 48% LL-D05139β by HPLC.

A second portion of (A) (676 mg) was chromatographed as described above, giving 176 mg of white powder (F) which was 34% LL-D05139β and 83 mg of pale yellow solids (G), which was 89% LL-D05139β.

Samples (B) (420 mg), (C) (147 mg) and 600 mg of product derived from another fermentation conducted as described in Example 2, were combined and chromatographed as described above, giving 262 mg of white powder (H) which was 33% LL-D05139β and 63 mg of pale yellow solids (J) which was 82% LL-D05139β.

Products (D), (F) and (H) were combined and chromatographed on a column of microcrystalline cellulose in the same manner as described above, giving 402 mg of white powder (K) which was 27% LL-D05139β and 80 mg of pale yellow solids (L) which was 100% LL-D05139β.

The analytical data for (L) were as follows:
Elemental analysis: C36.8; H,5.2; N,19.6;
Molecular weight: 244 (FAB-MS);
Optical Rotation: $[\alpha]_D^{26} = +57° \pm 5°$(C,0.19%, Water);
UV$_{max}$ 250 nm (E$_{1cm}^{1\%}$ 646) (Spectrum as shown in FIG. I, methanol/water solution);
IR spectrum (KBr disc) as shown in FIG. II;
$^1$H NMR spectrum as shown in FIG. III (D$_2$O; ppm from TMS) 1.56(3H, d, J=7.4 Hz), 4.07(1H, q, J=7.4 Hz), 4.49(2-3H, m), 5.19(1H, broad s).

We claim:
1. A process for preparing antibiotic LL-D05139β which comprises cultivating *Glycomyces harbinensis*, gen. nov., sp. nov., having the identifying characteristics of NRRL 15337, and the antibiotic-producing mutants thereof, under aerobic conditions, in a sterile liquid medium containing assimilable sources of carbon, nitrogen and inorganic anion and cation salts, until substantial antibiotic activity is imparted to said medium by the production of LL-D05139β and then recovering the antibiotic therefrom.

2. A process for preparing antibiotic LL-D05139β which comprises aerobically fermenting a liquid medium containing assimilable sources of carbon, nitrogen and inorganic anion and cation salts, which medium has been inoculated with a viable culture of the organism *Glycomyces harbinensis*, gen. nov., sp. nov., having the identifying characteristics of NRRL 15337, and the antibiotic-producing mutants thereof, maintaining said fermentation culture with sterile aeration and agitation at pH 7–9.5, for a period of 90–200 hours at 24°–32° C., harvesting the mash and extracting the antibiotic.

3. The process according to claim 2, wherein the pH of the liquid medium is 7.4.

4. A biologically pure culture of the microorganism *Glycomyces harbinensis*, gen. nov., sp. nov., having the identifying characteristics of NRRL 15337, said culture being capable of producing the antibiotic LL-D05139β in recoverable quantity upon fermentation in an aqueous nutrient medium containing assimilable sources of carbon, nitrogen and inorganic anion and cation salts.

5. The biologically pure culture of the microorganism *Glycomyces harbinensis* according to claim 4, wherein said microorganism has spontaneously mutated, such that the microorganism is genetically altered but still retains the ability to synthesize antibiotic LL-D05139β.

6. The biologically pure culture of the microorganism *Glycomyces harbinensis* according to claim 4, wherein said microorganism has been subjected to mutagenic means such that the microorganism is genetically altered but still retains the ability to synthesize antibiotic LL-D05139β.

* * * * *